United States Patent
Allard et al.

(10) Patent No.: US 8,292,930 B2
(45) Date of Patent: Oct. 23, 2012

(54) TETHERING DEVICES AND METHODS TO TREAT A SPINAL DEFORMITY

(75) Inventors: Randy N. Allard, Germantown, TN (US); Thomas A. Carls, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 834 days.

(21) Appl. No.: 12/116,016

(22) Filed: May 6, 2008

(65) Prior Publication Data
US 2009/0281575 A1    Nov. 12, 2009

(51) Int. Cl.
*A61B 17/70* (2006.01)
(52) U.S. Cl. ......... 606/278; 606/246; 606/263; 606/258
(58) Field of Classification Search ............ 606/57, 606/60, 74, 90, 102, 103, 105, 246–279
See application file for complete search history.

(56) References Cited

U.S. PATENT DOCUMENTS

| | | | |
|---|---|---|---|
| 4,078,559 A * | 3/1978 | Nissinen ................ | 606/258 |
| 4,573,454 A * | 3/1986 | Hoffman ................ | 606/250 |
| 4,998,936 A | 3/1991 | Mehdian | |
| 5,466,261 A | 11/1995 | Richelsoph | |
| 5,951,555 A | 9/1999 | Rehak et al. | |
| 6,086,590 A * | 7/2000 | Margulies et al. ........ | 606/263 |
| 6,277,120 B1 * | 8/2001 | Lawson ................ | 606/263 |
| 6,296,643 B1 | 10/2001 | Hopf et al. | |
| 6,299,613 B1 | 10/2001 | Ogilvie et al. | |
| 6,358,283 B1 | 3/2002 | Hogfors et al. | |
| 6,616,669 B2 | 9/2003 | Ogilvie et al. | |
| 6,623,484 B2 | 9/2003 | Betz et al. | |
| 7,708,765 B2 * | 5/2010 | Carl et al. ............... | 606/279 |
| 2003/0191470 A1 * | 10/2003 | Ritland ................... | 606/61 |
| 2004/0106921 A1 * | 6/2004 | Cheung et al. ............ | 606/61 |
| 2005/0216004 A1 | 9/2005 | Schwab | |
| 2005/0261770 A1 * | 11/2005 | Kuiper et al. ............ | 623/17.11 |
| 2006/0009767 A1 * | 1/2006 | Kiester ................... | 606/61 |
| 2006/0036256 A1 * | 2/2006 | Carl et al. ............... | 606/86 |
| 2006/0036259 A1 * | 2/2006 | Carl et al. ............... | 606/90 |
| 2006/0217715 A1 | 9/2006 | Serhan | |
| 2007/0073293 A1 | 3/2007 | Martz | |
| 2007/0288011 A1 | 12/2007 | Logan | |
| 2007/0288024 A1 * | 12/2007 | Gollogly ................ | 606/73 |
| 2008/0033436 A1 * | 2/2008 | Song et al. ............. | 606/61 |
| 2008/0045951 A1 | 2/2008 | Fanger et al. | |
| 2008/0177319 A1 * | 7/2008 | Schwab ................ | 606/257 |
| 2008/0195100 A1 * | 8/2008 | Capote et al. ........... | 606/71 |
| 2009/0204156 A1 * | 8/2009 | McClintock et al. ....... | 606/278 |

OTHER PUBLICATIONS

International Searching Authority, International Search Report and Written Opinion, Jan. 6, 2010.
Gruca, Adam, The Pathogenesis and Treatment of Idiopathic Scoliosis: A Preliminary Report, 1958; 40:570-584, The Journal of Bone and Joint Surgery, United States.

* cited by examiner

*Primary Examiner* — Alvin Stewart
*Assistant Examiner* — Michelle C Eckman

(57) ABSTRACT

The present application is directed to tethering systems that provide a corrective force to one or more vertebral members. The tethering systems may include an elongated member with first and second sections. The sections are displaceable relative to each other to increase a length of the elongated member. The first section may be attached to a first vertebral member, and a second section may be attached to a second vertebral member. At least one tether may be attached to the elongated member. The tether may include a length to be attached to the first and second sections, and to a third vertebral member that is positioned between and laterally offset from the first and second vertebral members. The length of the elongated member may increase thus causing the tether to apply a corrective force to the third vertebral member.

20 Claims, 7 Drawing Sheets

TETHERING DEVICES AND METHODS TO TREAT A SPINAL DEFORMITY

BACKGROUND

The present application is directed to devices and methods for treating a spinal deformity and, more particularly, to tethering devices and methods that apply a corrective force to one or more vertebral members.

The spine is divided into four regions comprising the cervical, thoracic, lumbar, and sacrococcygeal regions. Vertebral members of the spine are aligned in a curved configuration that includes a cervical curve, thoracic curve, and lumbosacral curve. Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members. One or more tethers may be attached to the vertebral members to reduce and/or eliminate the deformity.

Tethering is often used with patients with growth potential of the bony members including prepubescent children less than ten years old who have yet to experience a growth spurt, and adolescents from 10-12 years old with continued growth potential. The tethering system should accommodate the expected continued growth of the patient after the implantation. Damage to the patient and/or the tethering system could occur if the system is not able to accommodate this growth.

SUMMARY

The present application is directed to tethering systems that provide a corrective force to one or more vertebral members. The tethering systems may include an elongated member with first and second sections. The sections are displaceable relative to each other to increase a length of the elongated member. The first section may be attached to a first vertebral member, and a second section may be attached to a second vertebral member. At least one tether is attached to the elongated member. The tether includes a length to be attached to the first and second sections, and to a third vertebral member that is positioned between and laterally offset from the first and second vertebral members. The length of the elongated member may increase thus causing the tether to apply a corrective force to the third vertebral member.

The aspects of the various embodiments may be used alone or in any combination, as is desired.

DETAILED DESCRIPTION

Figure 1:
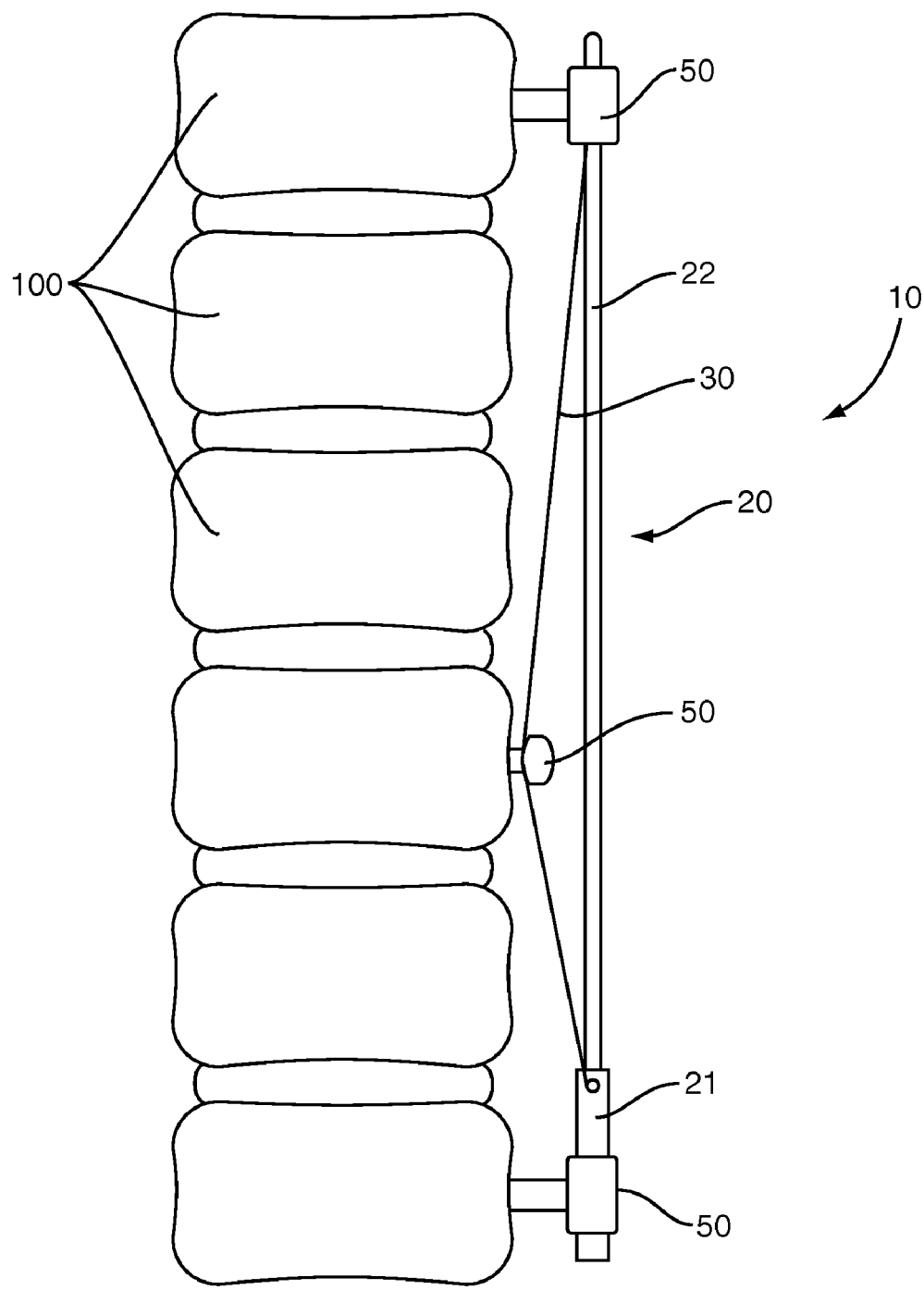
FIG. 1 is a schematic view of a tethering system attached to vertebral members according to one embodiment.

The present application is directed to tethering devices and methods for applying a corrective force to one or more vertebral members. FIG. 1 illustrates a schematic representation of one embodiment of the tethering device 10 that includes an elongated member 20 that is attached with anchors 50 to vertebral members 100. The elongated member 20 includes first and second sections 21, 22 that are movably connected together to allow for increasing the length during growth of the patient. A tether 30 is connected to each of the sections 21, 22 and further is connected by an anchor 50 to a misaligned vertebral member 100. As the patient grows and the length of the elongated member 20 increases, the tether 30 applies a corrective force towards the elongated member 20 on the misaligned vertebral member 100.

Figure 2:
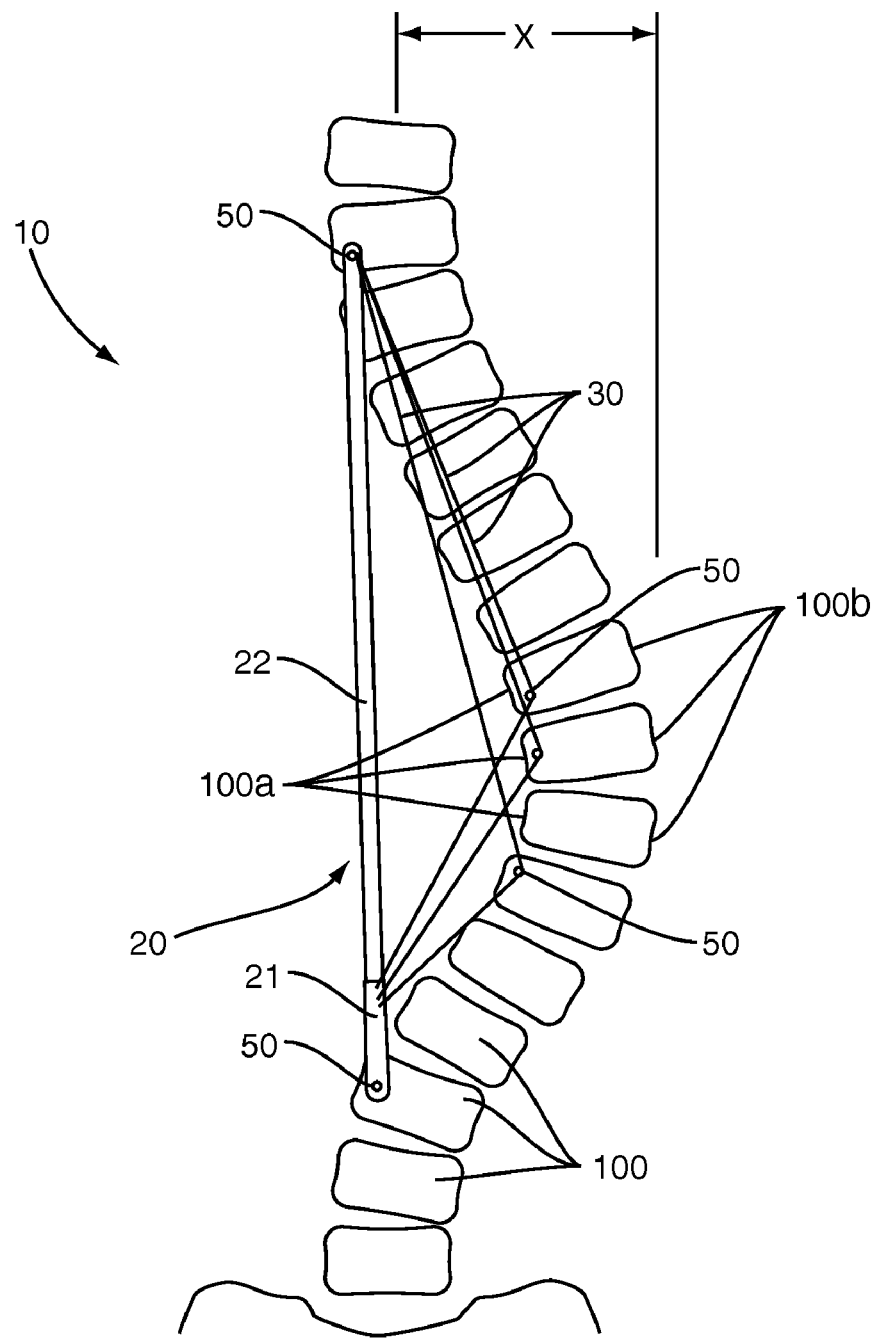
FIG. 2 is a schematic view of a tethering system attached to vertebral members according to one embodiment.

The tethering devices 10 may be used for treating a variety of ailments within the patient. FIG. 2 illustrates one embodiment for treating a scoliotic spine. This spine has a scoliotic curve with an apex of the curve being offset a distance X from its correct alignment in the coronal plane. The spine is deformed laterally so that the axes of the vertebral members 100 are displaced from the sagittal plane passing through a centerline of the patient. In the area of the lateral deformity, each of the vertebral members 100 includes a concave side 100a and a convex side 100b. In this embodiment, the device 10 extends along the concave side 100a of two or more adjacent vertebral members 100. The device 100 applies a force to pull the vertebral members 100 into alignment to treat the deformity.

The elongated member 20 has a length to extend along the spine and includes a first section 21, and a second section 22. The elongated member 20 is constructed to allow relative movement between the members 21, 22. The first section 21 is attached to an inferior vertebral member 100 and the second section 22 to a superior vertebral member 100. In this embodiment, the elongated member 20 includes a length to extend along the spine across a majority of the spinal deformity. In other embodiments, the elongated member 20 includes a length that is less than the spinal deformity.

Figure 10:
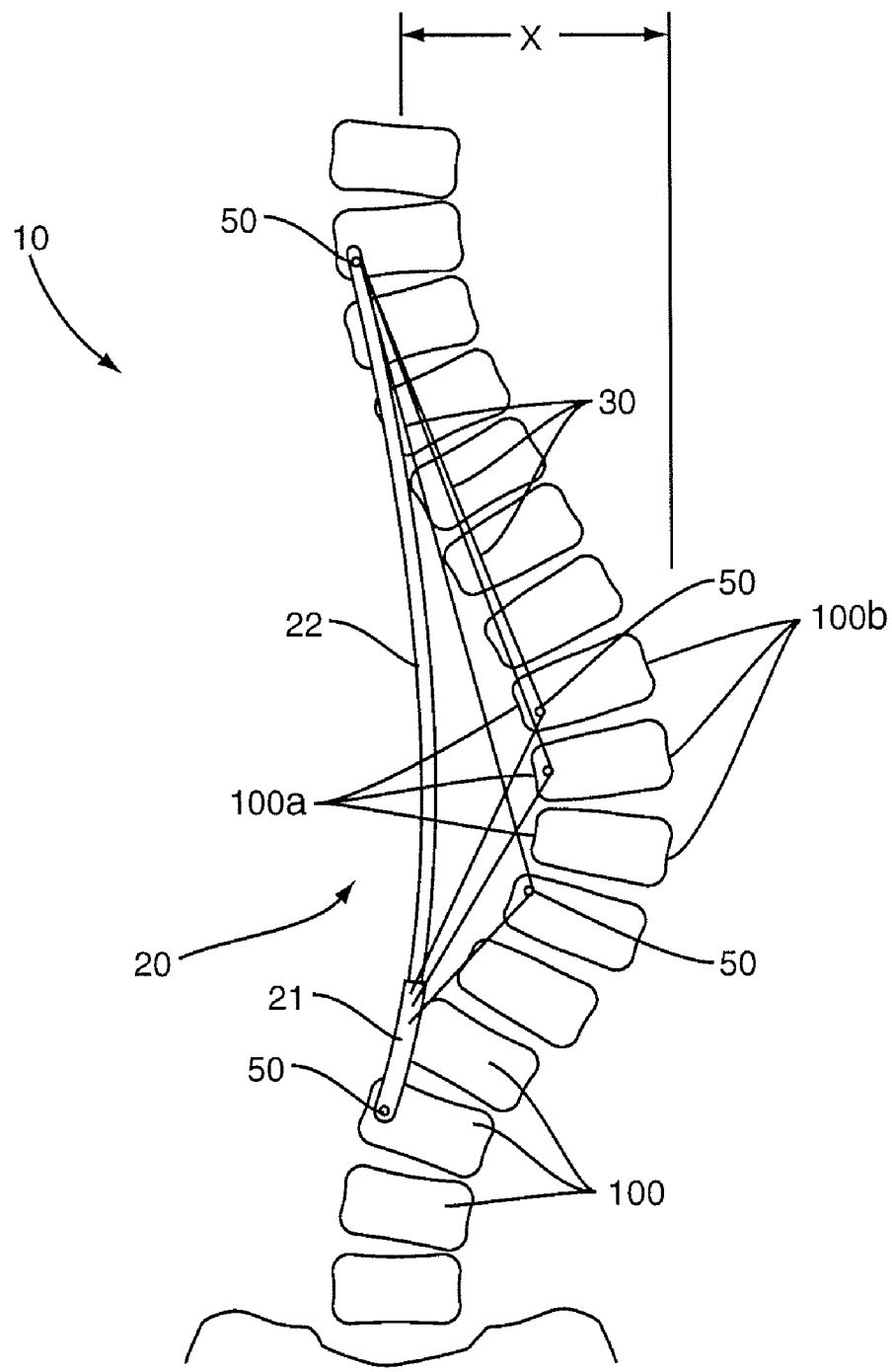
FIG. 10 is a schematic view of a tethering system attached to vertebral members according to one embodiment.

In one embodiment, the elongated member 20 includes first and second sections 21, 22 that are each substantially straight as illustrated in FIG. 2. A longitudinal axis extends through the elongated member 20, and the sections 21, 22 move along the axis as the length of the elongated member 20 changes. In other embodiments, one or both of the sections 21, 22 are curved as illustrated in FIG. 10.

Figure 3:
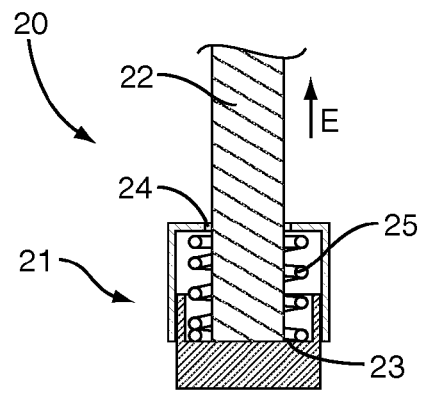
FIG. 3 is a sectional view of a portion of an elongated member according to one embodiment.

The elongated member 20 includes the second section 22 being movable relative to the first section 21. FIG. 3 includes one embodiment of an elongated member 20 with the first section 21 including an opening 24 sized to extend around a portion of the second section 22. A biasing member 25 is positioned between the first and second sections 21, 22. The force applied by the biasing member 25 forces the second section within the first section 22. The force of the biasing member 25 is overcome as the patient grows allowing the second section 22 to move away from the first section 21 in the direction indicated by arrow E. In this embodiment, a flange 23 with a width greater than the opening 24 is positioned on the second section 22 to prevent the second section 22 from becoming detached from the first section 21. A variety of biasing members 25 may be used to bias the second section 22 towards the first section 21. Examples include but are not limited to a spring and a flexible material such as stainless steel, titanium, memory polymer, and memory metal.

Figure 4:
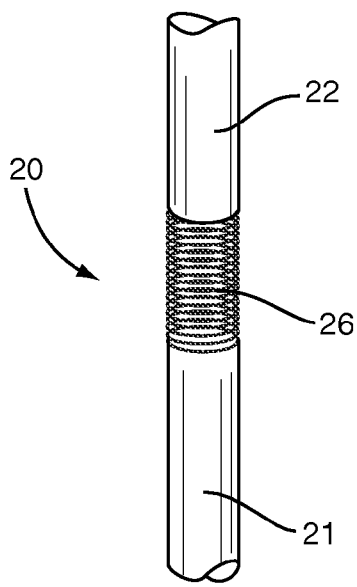
FIG. 4 is a perspective view of an elongated member according to one embodiment.
Figure 5:
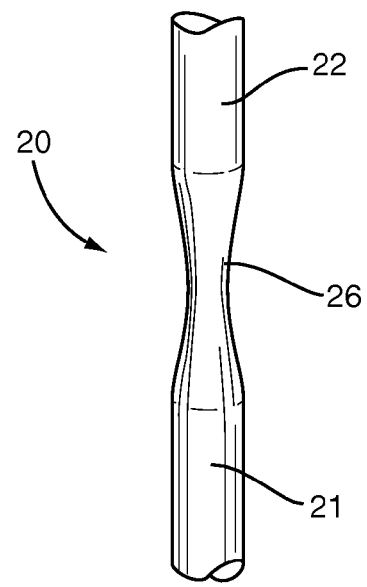
FIG. 5 is a perspective view of an elongated member according to one embodiment.

FIGS. 4 and 5 illustrate other embodiments of the elongated member 20 that each includes an expandable section 26 positioned between the first and second sections 21, 22. The expandable section 26 of FIG. 4 includes a plurality of coils formed within the member 20. The coils 26 separate when the patient grows to increase the length of the elongated member 20. FIG. 4 includes the elongated member 20 including a unitary, one-piece construction. In a similar embodiment, the expandable section is a separate piece that is attached to the first and second sections 21, 22. The expandable section 26 of FIG. 5 includes a reduced width compared to the first and second sections 21, 22. In this embodiment, the expandable section 26 is constructed of a deformable material, such as polymers and elastomers. In another embodiment, the flexible section 26 may include a different cross-sectional shape than the first and second section 21, 22 that provides for expansion. In one embodiment, the entire elongated member 20 includes a uniform shape and size and is constructed from a deformable material that allows for an increase in the length as the patient grows. The embodiment of FIG. 5 includes the elongated member 20 constructed as a unitary, one-piece embodiment. In another embodiment, the expandable section 26 is formed by either a deformable material or a section with a different cross-sectional shape and is a separate piece that is attached between the first and second sections 21, 22.

A variety of different tethers 30 may be used for treating the spinal deformity. Embodiments include but are not limited to cables, artificial or synthetic strands, rods, plates, and springs. In one embodiment, the tethers 30 comprise an inner core with an outer sheath. The inner core and outer sheath may be made of a braided polymer such as polyester, polypropylene, or polyethylene. In one specific embodiment, the inner core and outer sheath are both made of polyethylene with the inner core being braided for strength and the outer sheath being braided for abrasion resistance. In one embodiment with the tether 30 being a strand, the strand may be manufactured from a variety of materials, including, but not limited to, conventional biocompatible implant alloys such as titanium, stainless steel, cobalt-chrome alloys, or even shape memory alloys and materials such as nickel-titanium. In the embodiments with multiple tethers 30, the tethers 30 may include the same or different construction.

The tethers 30 are attached to the first section 21 and to the second section 22. The tethers 30 include a length to also be attached to one or more misaligned vertebral members 100. In one embodiment, the ends of the tethers 30 are attached to each section 21, 22. In another embodiment, a section inward from the ends is attached to the sections 21, 22. In embodiments with multiple tethers 30, each individual tether 30 may be attached at the same location on the first section 21 and the second section 22. Alternatively, the tethers 30 may be attached along a length of one or both sections 21, 22.

Figure 6:
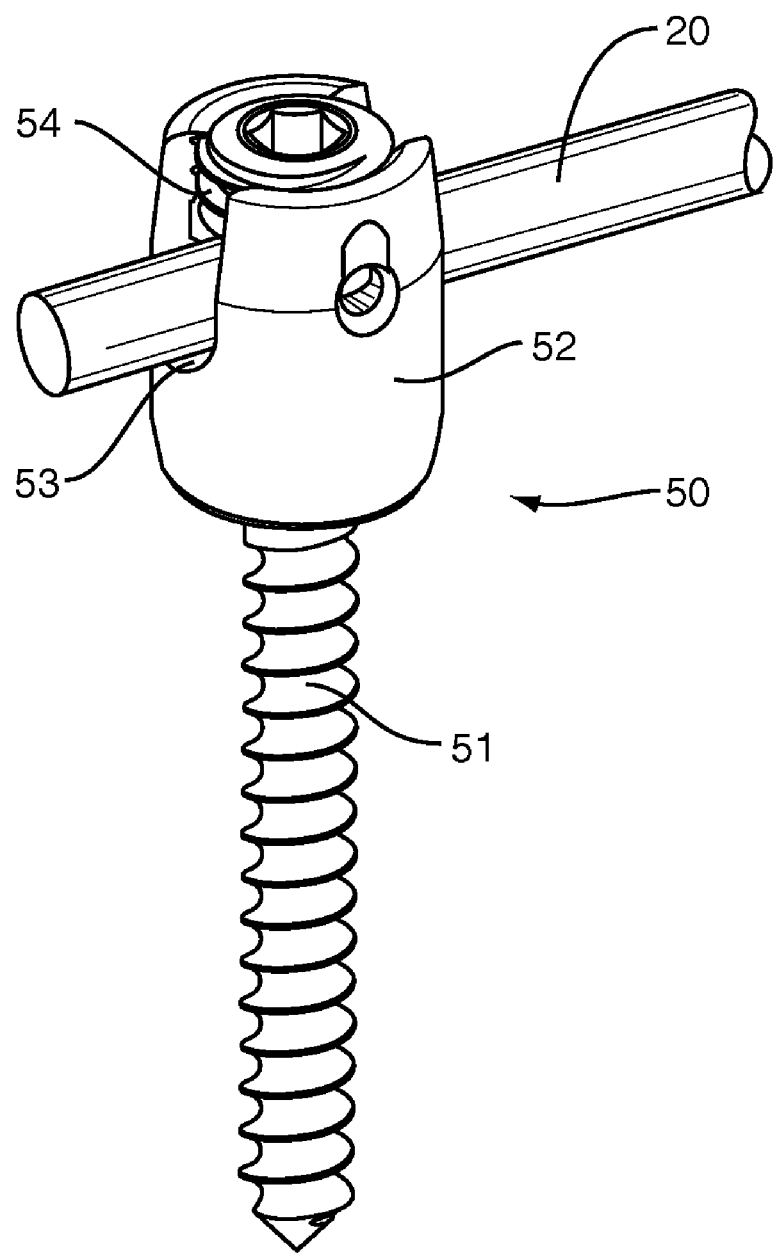
FIG. 6 is a perspective view of an anchor according to one embodiment.

Various anchors 50 may be used to attach the tether 30 and elongated member 20 to the vertebral members 100. FIG. 6 includes one embodiment of an anchor 50 that includes a shaft 51 sized to extend into the vertebral member 100. A receiver 52 is positioned at an end of the shaft 51 and includes a channel 53 sized to receive the elongated member 20 or tether 30. A fastener 54 may be attachable to the receiver 52 to capture the elongated member 20 or tether 30 in the channel 53 and prevent escape. The receiver 52 may be fixedly attached to the shaft 51, or may be movable relative to the shaft 51.

Figure 7:
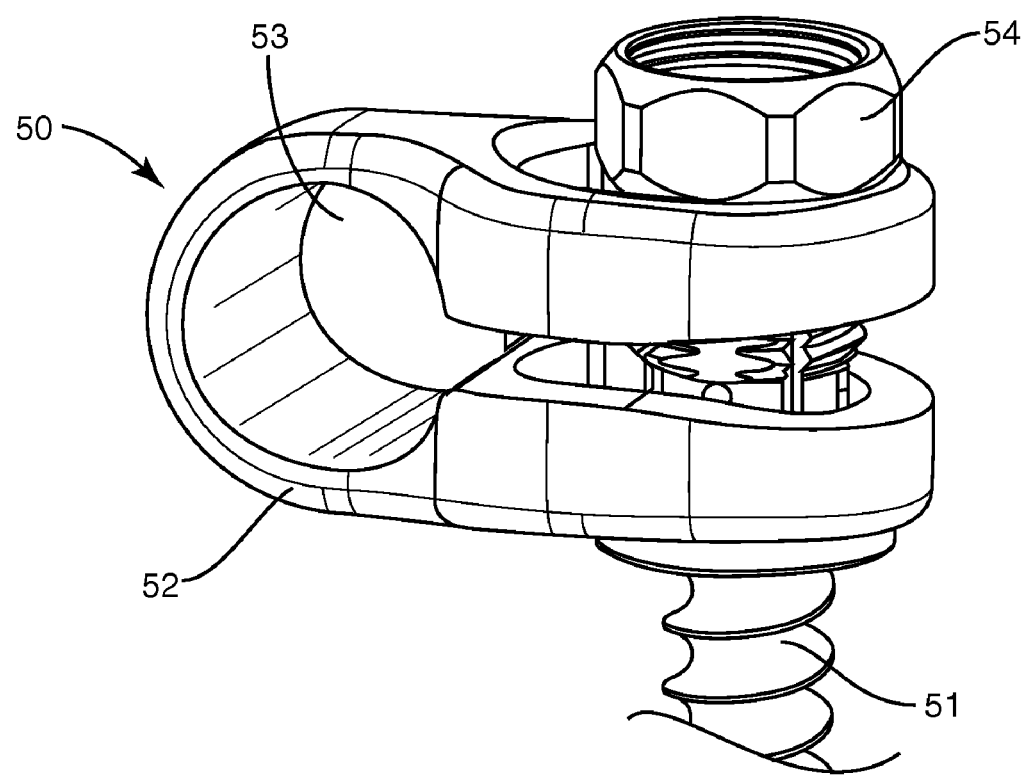
FIG. 7 is a perspective view of an anchor according to one embodiment.
Figure 8:
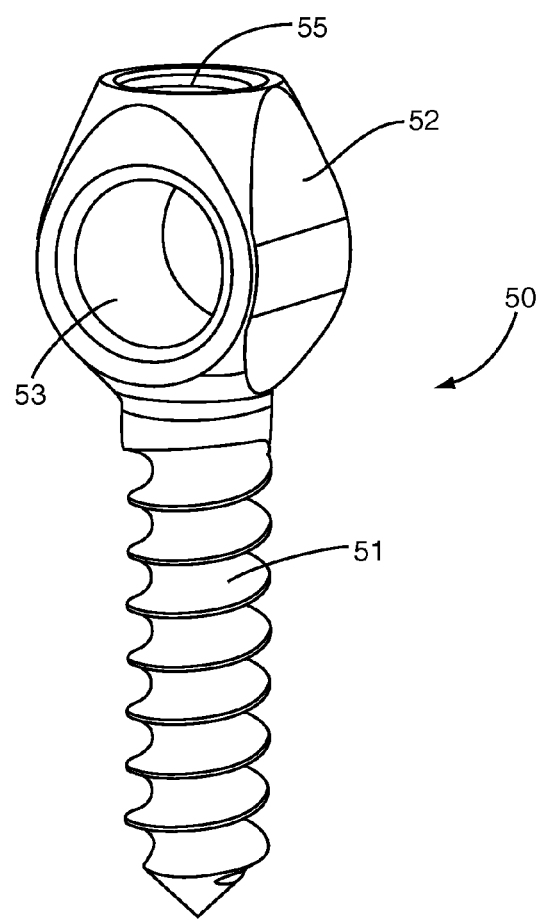
FIG. 8 is a perspective view of an anchor according to one embodiment.
Figure 9:
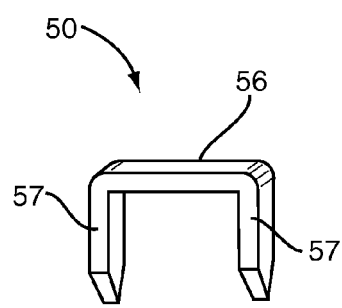
FIG. 9 is a perspective view of an anchor according to one embodiment.

FIG. 7 illustrates another anchor 50 embodiment with the receiver 52 including a channel 53 that is laterally offset from the shaft 51. The channel 53 is again sized to receive the elongated member 20 or tether 30. The fastener 54 attaches to the end of the shaft 51 and compresses together the arms of the receiver 52 to prevent escape of the elongated member 20 or tether 30. FIG. 8 includes another anchor 50 with the receiver 52 including an enclosed channel 53. The receiver 52 may include an opening 55 into the channel 53. The opening 55 is sized to receive a fastener (not illustrated) that would extend into the channel 53 to engage the elongated member 20 or tether 30. FIG. 9 includes another anchor 50 in the form of a staple with a base 56 and a pair of legs 57. The legs 57 are positioned in the vertebral member 100, and the base 56 extends across the elongated member 20 or tether 30.

The anchors 50 that attach the elongated member 20 to the vertebral members 100 may be the same or different than the anchors 50 that are attached to the tethers 30.

In one embodiment of using the tethering device 10, the elongated member 20 is attached to the vertebral members 100. This includes the first section 21 attached to a first vertebral member (e.g., an inferior vertebral member 100) and the second section 22 attached to a second vertebral member (e.g., a superior vertebral member 100). The elongated member 100 initially includes a length such that the first and second vertebral members 100 are spaced by one or more intermediate vertebral members 100. As best illustrated in FIG. 2, at least one intermediate vertebral member 100 is laterally misaligned from an axis formed between the anchors 50 that attaches the elongated member 20 to the vertebral members 100.

One or more tethers 30 are attached to the elongated member 20. An intermediate part of the tethers 30 is attached to the vertebral members 100. In one embodiment as illustrated in FIG. 2, each tether 30 is attached to just one vertebral member 100. In another embodiment (not illustrated), one or more of the tethers 30 is attached to two or more vertebral members 100.

The tethers 30 are attached to the vertebral members 100 with anchors 50. In one embodiment, the anchors 50 prevent the tethers 30 from sliding through the anchors 50. In another embodiment, the anchors 50 allow the tethers 30 to slide through the anchors 50 as the patient grows.

As the patient grows, the elongated member 20 increases in length as the first and second sections 21, 22 move apart. This increase causes the tethers to apply a corrective force to the misaligned vertebral members 100 to which they are attached. This force pulls the vertebral members 100 towards the elongated member 20. In one embodiment, the force applied to the misaligned vertebral members 100 increases the more the patient grows.

In one embodiment, the elongated member 20 increases in length due to the growth of the patient. Other aspects may also cause the elongated member 20 to increase in length, such as correction of the spinal deformity. Therefore, the tethering system 10 may be used with patients other than those that will experience spinal growth.

The tethering device 10 may be used to treat a wide variety of ailments. One type includes spinal deformities. The primary indications will be progressive idiopathic scoliosis with or without sagittal deformity in either infantile or juvenile patients. One patient population upon which to practice these embodiments is prepubescent children (before growth spurt) less than ten years old. Other patient groups upon which the embodiments may be practiced include adolescents from 10-12 years old with continued growth potential. It should be understood that fusionless tethering may also be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. In one embodiment, the tethering device 10 is implanted with an anterior, minimally invasive (thoracoscopic) procedure on the convex side of the spinal curve. The tethering system 10 may be delivered into the patient in a minimally invasive approach using thoracoscopic instrumentation. The tethering device 10 may also be delivered in a posterior procedure, or some combination of both anterior and posterior. Finally, it should be understood that if the procedure fails to correct the curve but does, in fact, prevent further progression (which includes increase in the magnitude of the curve) it can and should be considered successful.

It should be understood that scoliosis is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A tethering device to treat a spinal deformity comprising:
   a variable length elongated member with first and second sections, the elongated member having an expandable section to allow the elongated member to be extendable from a first length to a second length with the first section being displaceable away from the second section, said expandable section comprising coils defined by a helically wound material having a uniform cylindrical cross section, the coils being configured to separate as a patient grows, wherein the first section, the second section and the coils each have the same diameter;
   a tether attached at a first point to the first section and attached at a second point to the second section;
   an axis extending directly between the first and second points, the first and second points being spaced apart along the axis by a first distance;
   the tether including a length that is greater than the first distance to attach to a vertebral member that is offset from the axis;
   the tether configured to apply a force towards the axis when the elongated member moves from the first length towards the second length.

2. The tethering device of claim 1, wherein an intermediate section of the elongated member is positioned away from the axis and ends of the elongated member are positioned on the axis.

3. The tethering device of claim 1, further comprising a second tether that is attached to the first section and the second section, the second tether being longer than the first distance to attach to a second vertebral member that is offset from the axis, the tether and the second tether each extending outward on a single side of the elongated member.

4. The tethering device of claim 3, wherein the second tether is attached to the first section at the first point and to the second section at the second point.

5. The tethering device of claim 3, further comprising a third tether that is attached to the first section and the second section, the third tether being longer than the first distance to attach to a third vertebral member that is offset from the axis, the third tether extending outward on the same single side of the elongated member as the tether and the second tether.

6. The tethering device of claim 1, wherein the coils each extend along an axis between a first end and a second end and include a hollow center extending parallel to the axis.

7. The tethering device of claim 1, wherein at least one of the first and second sections are curved.

8. The tethering device of claim 1, wherein the elongated member includes a unitary, one-piece construction.

9. The tethering device of claim 1, wherein the expandable section is a separate piece that is attached to the first and second sections.

10. The tethering device of claim 1, wherein the first and second sections each have a diameter that is equivalent to a diameter of the expandable section.

11. The tethering device of claim 1, wherein the tether comprises an inner core and an outer sheath each made of a polymer comprising polyester, polypropylene, or polyethylene.

12. A tethering device to treat a spinal deformity comprising:
   a variable length elongated member with first and second sections and an intermediate section positioned between the first and second sections, the intermediate section comprising an expandable section having a continuously narrowing diameter compared to the first and second sections and being more deformable than the first and second sections, the elongated member being extendable from a first length to a second length with the first section displaced away from the second section, wherein the first and second sections maintain a uniform diameter,
   a third point positioned between and laterally offset from first and second points, the first and second points positioned on the elongated member;

a tether attached at the first point to the first section and attached at the second point to the second section, the tether including a length to extend to the third point;

the second section being displaceable away from the first section to apply a force to the third point through the tether to cause the third point to move towards an axis formed directly between the first and second points.

13. The tethering device of claim 12, wherein the elongated member includes a curved shape.

14. The tethering device of claim 12, wherein the elongated member includes a unitary, one-piece construction.

15. The tethering device of claim 12, further comprising a second tether attached to the first section and the second section and extending to the third point, each of the tether and the second tether extending outward on a same side of the elongated member.

16. The tethering device of claim 12, wherein the tether comprises an inner core and an outer sheath each made of a polymer comprising polyester, polypropylene, or polyethylene.

17. The tethering device of claim 12, wherein at least one of the first and second sections are curved.

18. A tethering device to treat a spinal deformity comprising:

a variable length elongated member with first and second sections and an expandable section comprising a deformable material having a continuously narrowing diameter and a different cross sectional shape compared to the first section and the second section, the expandable section being positioned between the first section and the second section, the elongated member including a longitudinal axis that extends through the first and second sections;

a plurality of tethers each including a first end attached to the first section and a second end attached to the second section, each of the plurality of tethers including an intermediate part positioned between the first and second ends that is adapted to be attached to a different vertebral member that is offset from the longitudinal axis;

each of the plurality of tethers configured to apply a force towards the axis when the elongated member moves from the first length towards the second length.

19. The tethering device of claim 18, wherein the first ends of each of the plurality of tethers is attached to a common point on the first section of the elongated member.

20. The tethering device of claim 18, wherein the elongated member and the plurality of tethers are configured for the force applied to the offset vertebral members to increase as the length of the elongated member increases.

* * * * *